(12) United States Patent
Kitamura et al.

(10) Patent No.: US 9,629,895 B2
(45) Date of Patent: Apr. 25, 2017

(54) METHOD FOR PREVENTION OR TREATMENT OF INTRACTABLE INFLAMMATORY BOWEL DISEASE

(75) Inventors: Kazuo Kitamura, Miyazaki (JP); Shinya Ashizuka, Miyazaki (JP); Haruhiko Inatsu, Miyazaki (JP); Toshihiro Kita, Miyazaki (JP)

(73) Assignee: University of Miyazaki, Miyazaki (JP)

( * ) Notice: Subject to any disclaimer, the term of this patent is extended or adjusted under 35 U.S.C. 154(b) by 0 days.

(21) Appl. No.: 13/979,048

(22) PCT Filed: Jan. 12, 2012

(86) PCT No.: PCT/JP2012/051010
§ 371 (c)(1),
(2), (4) Date: Jul. 10, 2013

(87) PCT Pub. No.: WO2012/096411
PCT Pub. Date: Jul. 19, 2012

(65) Prior Publication Data
US 2013/0296260 A1    Nov. 7, 2013

Related U.S. Application Data

(60) Provisional application No. 61/431,975, filed on Jan. 12, 2011.

(51) Int. Cl.
*A61K 38/17*    (2006.01)
*A61K 38/22*    (2006.01)

(52) U.S. Cl.
CPC .............. *A61K 38/17* (2013.01); *A61K 38/22* (2013.01)

(58) Field of Classification Search
None
See application file for complete search history.

(56) References Cited

U.S. PATENT DOCUMENTS 5,639,855 A * 6/1997 Kitamura et al. ............ 530/324

FOREIGN PATENT DOCUMENTS

| JP | 2004-244378 A | 9/2004 |
| JP | 2006-290777 | * 10/2006 |
| JP | 2006-290777 A | 10/2006 |
| WO | WO-2012/096411 A1 | 7/2012 |

OTHER PUBLICATIONS

Merriam Webster Dictionary (downloaded Apr. 30, 2014 from http://www.merriam-webster.com/dictionary/difficult).*
Charles et al (Am J Physiol Regulatory Integrative Comp Physiol (2001) 281: R1887-R1894).*
Nemours Foundation ("Inflammatory Bowel Disease" https://web.archive.org/web/20091109054750/http://kidshealth.org/parent/medical/digestive/ibd.html# (Nov. 9, 2009) downloaded May 13, 2014).*
Meeran et al (J Clin Endorcrinol Metab (Jan. 1997) 82(1): 95-100).*
Farrell et al (Journal of Endocrinology (2003) 178:339-346).*
Charles et al (Am J Physiol Regulatory Integrative Comp Physiol (2001) 281 R1887-R1894).*
Hart et al (Ailment Pharmacol Ther (Sep. 2010) 32(5): 615-627).*
Nemours Foundation ("Inflammatory Bowel Disease"https://web.archive.org/web/20091109054750/http://kidshealth.org/parent/medical/digestive/ibd.html# (Nov. 9, 2009) downloaded May 13, 2014).*
Meeran et al (J Clin Endorcrinol Metab (Jan. 1997) 82(1 ): 95-100).*
Rademaker et al (Hypertension (2002) 40: 667-672).*
Mayo Clinic Chrohn's Disease—Definition (downloaded on Oct. 16, 2015 from http://www.mayoclinic.org/diseases-conditions/crohns-disease/basics/definition/CON-20032061).*
Mayo Clinic Chrohn's Disease—Causes (downloaded on Oct. 16, 2015 from http://www.mayoclinic.org/diseases-conditions/crohns-disease/basics/causes/con-20032061).*
Mohamed et al (Healthline, "Inflammatory Bowel Disease" downloaded from http://www.healthline.com/health/inflammatory-bowel-disease#Treatment8 on Oct. 16, 2015).*
Wood (Science Life, The University of Chicago Medicine & Biological Sciences, downloaded from http://sciencelife.uchospitals.edu/2015/03/06/why-havent-we-cured-inflammatory-bowel-disease/ on Oct. 16, 2015).*
Ashizuka S., Inagaki-Ohara K., Kuwasako K., Kato J., Inatsu H., Kitamura K.; Adrenomedullin treatment reduces intestinal inflammation and maintains epithelial barrier function in mice administered dextran sulphate sodium., Microbiol Immunol. Oct. 2009; 53(10): 573-81.
Ashizuka S., Ishikawa N., Kato J., Yamaga J., Inatsu H., Eto T., Kitamura K.; Effect of adrenomedullin administration on acetic acid-induced colitis in rats., Peptides. Dec. 2005; 26(12): 2610-5. Epub Jun. 23, 2005.
Gonzales-Rey E., Fernandez-Martin A., Chorny A., et al.; Therapeutic effect of urocortin and adrenomedullin in a murine model of Crohn's disease., Gut 2006; 55: 824-832.
Talero E., Sánchez-Fidalgo S., de la Lastra CA, et al.; Acute and chronic responses associated with adrenomedullin administration in experimental colitis., Peptides. 2008; 29: Dec. 2001.

(Continued)

*Primary Examiner* — Marcela M Cordero Garcia
*Assistant Examiner* — Catherine Mader
(74) *Attorney, Agent, or Firm* — McCarter & English, LLP

(57) ABSTRACT

An object of the present invention is to provide methods for preventing or treating a steroid-resistant or steroid-dependent inflammatory bowel disease. The object can be achieved by a method for preventing or treating a steroid-resistant or steroid-dependent inflammatory bowel disease in a patient in need of the prevention or treatment of the inflammatory bowel disease, comprises administering an effective amount of adrenomedullin, a modified product thereof having an activity of suppressing steroid-resistant or steroid-dependent inflammation, or a salt thereof having an activity of suppressing steroid-resistant or steroid-dependent inflammation, to the patient.

10 Claims, 6 Drawing Sheets
(6 of 6 Drawing Sheet(s) Filed in Color)

(56) References Cited

OTHER PUBLICATIONS

Farrell RJ and Kelleher D. Glucocorticoid resistance in inflammatory bowel disease, J. Endocrinol., Sep. 2003, vol. 178, No. 3, pp. 339-346.

Nagatsugu Shiga et al; IBD Chiryo no. Okeru Steroid no. Shiyoho; IBD Research, 2009, vol. 3, No. 2I pp. 139-143.

Charles CJ et al., Comparative actions of adrenomedullin and nitroprusside: interactions with ANG II and norepinephrine; Am J Physiol Regul Integr Comp Physiol., Dec. 2012, vol. 281, No. 6, pp. 1887-1894.

Yasuo Suzuki; Nihon Shokaki byo Gakkai Zasshi, Dec. 2011, vol. 108, pp. 1977-1982.

International Search Report for PCT/JP2012/051010, Japanese Patent Office, mailed Feb. 14, 2012.

International Preliminary Report on Patentability, Japanese Patent Office, report completed Dec. 17, 2012.

International Preliminary Report on Patentability, Japanese Patent Office, report completed Dec. 17, 2012, English translation.

Nagatsugu Shiga et al; IBD Chiryo ni Okeru Steroid ni Shiyoho; IBD Research, 2009, vol. 3, No. 2, pp. 139-143.

Charles CJ et al., Comparative actions of adrenomedullin and nitroprusside: interactions with ANG II and norepinephrine; Am J Physiol Regul Integr Comp Physiol., Dec. 2001, vol. 281, No. 6, pp. 1887-1894.

Kojima, Ryotoro, et al., "The New Experimental Ulcerative Colitis Model in Rats Induced by Subsorosal Injection of Acetic Acid", The Japanese Pharmacological Society, Folia Pharmacologica Japonica, 2001, vol. 118, No. 2 pp. 123-130.

\* cited by examiner

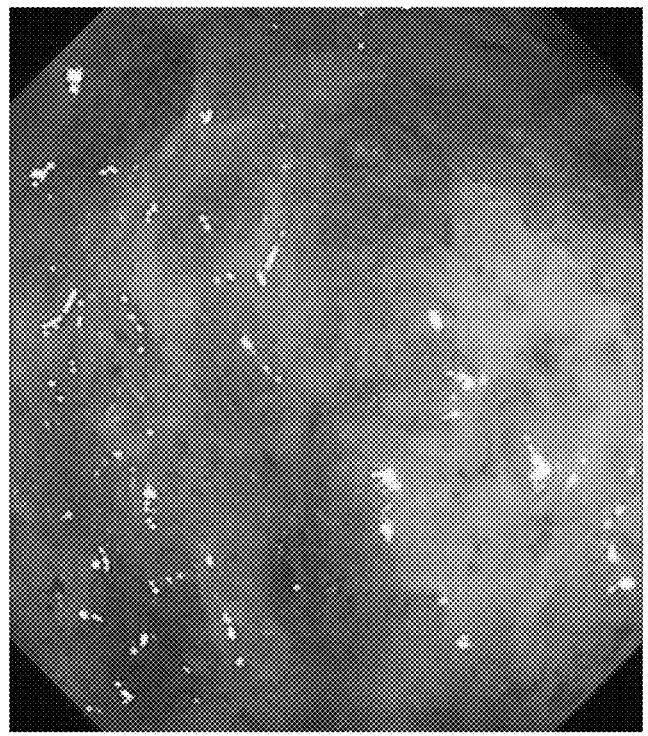
Fig. 1

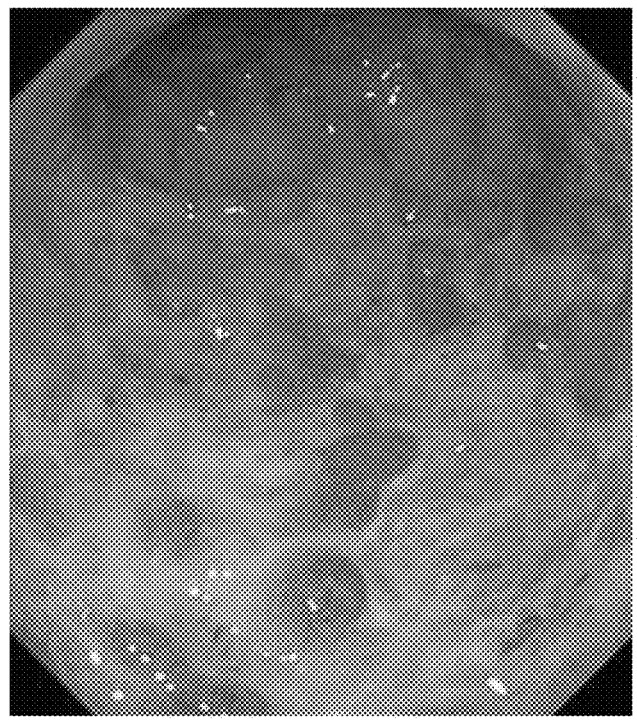
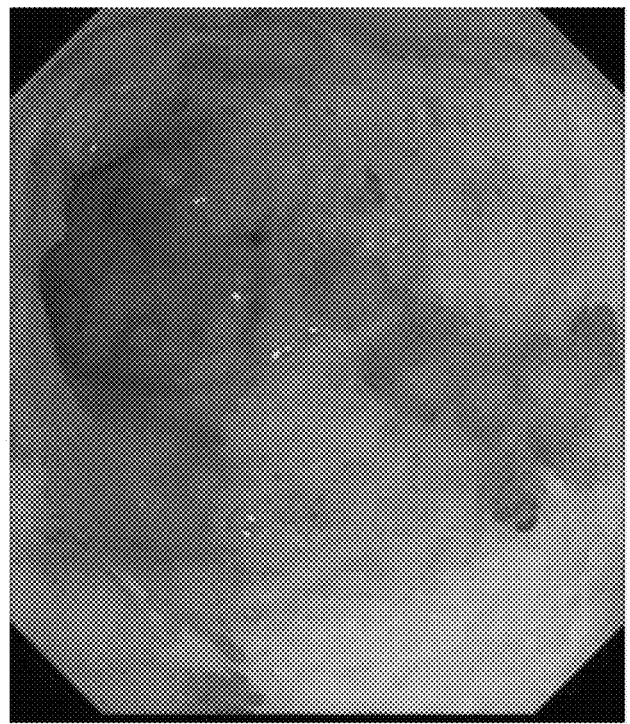
Fig. 3

SEQUENCE LISTING

<160> NUMBER OF SEQ ID NOS: 12

<210> SEQ ID NO 1
<211> LENGTH: 52
<212> TYPE: PRT
<213> ORGANISM: Homo sapiens

<400> SEQUENCE: 1

Tyr Arg Gln Ser Met Asn Asn Phe Gln Gly Leu Arg Ser Phe Gly Cys
 1               5                  10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 2
<211> LENGTH: 1449
<212> TYPE: DNA
<213> ORGANISM: Homo sapiens
<220> FEATURE:
<221> NAME/KEY: CDS
<222> LOCATION: (157)..(711)

<400> SEQUENCE: 2
ctggatagaa cagctcaagc cttgccactt cgggcttctc actgcagctg ggcttggact      60
tcggagtttt gccattgcca gtgggacgtc tgagactttc tccttcaagt acttggcaga    120
tcactctctt agcagggtct gcgcttcgca gccggg atg aag ctg gtt tcc gtc     174
                                        Met Lys Leu Val Ser Val
                                         1               5 gcc ctg atg tac ctg ggt tcg ctc gcc ttc cta ggc gct gac acc gct    222
Ala Leu Met Tyr Leu Gly Ser Leu Ala Phe Leu Gly Ala Asp Thr Ala
            10                  15                  20 cgg ttg gat gtc gcg tcg gag ttt cga aag aag tgg aat aag tgg gct    270
Arg Leu Asp Val Ala Ser Glu Phe Arg Lys Lys Trp Asn Lys Trp Ala
        25                  30                  35 ctg agt cgt ggg aag agg gaa ctg cgg atg tcc agc agc tac ccc acc    318
Leu Ser Arg Gly Lys Arg Glu Leu Arg Met Ser Ser Ser Tyr Pro Thr
    40                  45                  50 ggg ctc gct gac gtg aag gcc ggg cct gcc cag acc ctt att cgg ccc    366
Gly Leu Ala Asp Val Lys Ala Gly Pro Ala Gln Thr Leu Ile Arg Pro
55                  60                  65                  70 cag gac atg aag ggt gcc tct cga agc ccc gaa gac agc agt ccg gat    414
Gln Asp Met Lys Gly Ala Ser Arg Ser Pro Glu Asp Ser Ser Pro Asp
            75                  80                  85 gcc gcc cgc atc cga gtc aag cgc tac cgc cag agc atg aac aac ttc    462
Ala Ala Arg Ile Arg Val Lys Arg Tyr Arg Gln Ser Met Asn Asn Phe
        90                  95                 100 cag ggc ctc cgg agc ttt ggc tgc cgc ttc ggg acg tgc acg gtg cag    510
Gln Gly Leu Arg Ser Phe Gly Cys Arg Phe Gly Thr Cys Thr Val Gln
   105                 110                 115 aag ctg gca cac cag atc tac cag ttc aca gat aag gac aag gac aac    558
Lys Leu Ala His Gln Ile Tyr Gln Phe Thr Asp Lys Asp Lys Asp Asn
   120                 125                 130 gtc gcc ccc agg agc aag atc agc ccc cag ggc tac ggc cgc cgg cgc    606
Val Ala Pro Arg Ser Lys Ile Ser Pro Gln Gly Tyr Gly Arg Arg Arg
135                 140                 145                 150 cgg cgc tcc ctg ccc gag gcc ggc ccg ggt cgg act ctg gtg tct tct    654
Arg Arg Ser Leu Pro Glu Ala Gly Pro Gly Arg Thr Leu Val Ser Ser

|  |  |  |  |  |  |  |  |  |  |  |  |  |  |
|---|---|---|---|---|---|---|---|---|---|---|---|---|---|
|  |  |  | 155 |  |  |  | 160 |  |  |  | 165 |  |  |
| aag | cca | caa | gca | cac | ggg | gct | cca | gcc | ccc | ccg | agt | gga | agt gct ccc |
| Lys | Pro | Gln | Ala | His | Gly | Ala | Pro | Ala | Pro | Pro | Ser | Gly | Ser Ala Pro |
|  |  | 170 |  |  |  |  | 175 |  |  |  |  | 180 |  |

702 cac ttt ctt taggatttag gcgcccatgg tacaaggaat agtcgcgcaa     751
His Phe Leu
     185 gcatcccgct ggtgcctccc gggacgaagg acttcccgag cggtgtgggg accgggtctc     811 gacagccctg cggagaccct gagtccggga ggcaccgtcc ggcggcgagc tctggctttg     871 caagggcccc tccttctggg ggcttcgctt ccttagcctt gctcaggtgc aagtgcccca     931 gggggcgggg tgcagaagaa tccgagtgtt tgccaggctt aaggagagga gaaactgaga     991 aatgaatgct gagaccccccg gagcaggggt ctgagccaca gccgtgctcg cccacaaact     1051 gatttctcac ggcgtgtcac cccaccaggg cgcaagcctc actattactt gaactttcca     1111 aaacctaaag aggaaaagtg caatgcgtgt tgtacataca gaggtaacta tcaatattta     1171 agtttgttgc tgtcaagatt ttttttgtaa cttcaaatat agagatattt ttgtacgtta     1231 tatattgtat taagggcatt ttaaaagcaa ttatattgtc ctcccctatt ttaagacgtg     1291 aatgtctcag cgaggtgtaa agttgttcgc cgcgtggaat gtgagtgtgt ttgtgtgcat     1351 gaaagagaaa gactgattac ctcctgtgtg gaagaaggaa acaccgagtc tctgtataat     1411 ctatttacat aaaatgggtg atatgcgaac agcaaacc     1449

<210> SEQ ID NO 3
<211> LENGTH: 52
<212> TYPE: PRT
<213> ORGANISM: Sus scrofa

<400> SEQUENCE: 3

Tyr Arg Gln Ser Met Asn Asn Phe Gln Gly Leu Arg Ser Phe Gly Cys
1                5                  10               15

Arg Phe Gly Thr Cys Thr Val Gln Lys Leu Ala His Gln Ile Tyr Gln
               20                  25                  30

Phe Thr Asp Lys Asp Lys Asp Gly Val Ala Pro Arg Ser Lys Ile Ser
         35                  40                  45

Pro Gln Gly Tyr
    50

<210> SEQ ID NO 4
<211> LENGTH: 1493
<212> TYPE: DNA
<213> ORGANISM: Sus scrofa

<400> SEQUENCE: 4
gcggaacagc tcgagccttg ccacctctag tttcttacca cagcttggac gtcggggttt     60
tgccactgcc agagggacgt ctcagacttc atcttcccaa atcttggcag atcacccccct     120 tagcagggtc tgcacatctc agccgggatg aagctggttc ccgtagccct catgtacctg     180
ggctcgctcg ccttcctggg cgctgacaca gctcggctcg acgtggcggc agagttccga     240
aagaaatgga ataagtgggc tctaagtcgt ggaaaaagag aacttcggct gtccagcagc     300
taccccaccg ggatcgccga cttgaaggcc gggcctgccc agactgtcat tcggccccag     360
gatgtgaagg ctcctctccg cagcccccag gccagcattc cggatgcagc ccgcatccga     420
gtcaagcgct accgcagag tatgaacaac ttccagggcc tgcggagctt cggctgtcgc     480
tttgggacgt gcaccgtgca aagctggcg caccagatct accagttcac ggacaaagac     540

```
aaggacggcg tcgcccccg  gagcaagatc agcccccagg gctacggccg ccggcgccga    600
cgctctctgc ccgaagccag cctgggccgg actctgaggt cccaggagcc acaggcgcac    660
ggggccccgg cctccccggc gcatcaagtg ctcgccactc tctttaggat ttaggcgcct    720
actgtggcag cagcgaacag tcgcgcatgc atcatgccgg cgcttcctgg ggcgggggc     780 ttcccggagc cgagcccctc agcggctggg gcccgggcag agacagcatt gagagaccga    840
gagtccggga ggcacagacc agcggcgagc cctgcatttt caggaacccg tcctgcttgg    900
aggcagtgtt ctcttcggct taatccagcc cgggtccccg ggtgggggtg gagggtgcag    960
aggaatccaa aggagtgtca tctgccaggc tcacggagag gagaaactgc gaagtaaatg   1020
cttagacccc cagggcaag  ggtctgagcc actgccgtgc cgcccacaaa ctgatttctg   1080
aaggggaata accccaacag ggcgcaagcc tcactattac ttgaactttc caaaacctag   1140
agaggaaaag tgcaatgtat gttgtatata aagaggtaac tatcaatatt taagtttgtt   1200
gctgtcaaga ttttttttg  taacttcaaa tatagagata ttttgtacg  ttatatattg   1260 tattaagggc attttaaaac aattgtattg ttcccctccc ctctatttta atatgtgaat   1320
gtctcagcga ggtgtaacat tgtttgctgc gcgaaatgtg agagtgtgtg tgtgtgtgtg   1380
cgtgaaagag agtctggatg cctcttgggg aagaagaaaa caccatatct gtataatcta   1440
tttacataaa atgggtgata tgcgaagtag caaaccaata aactgtctca atg          1493
```

<210> SEQ ID NO 5
<211> LENGTH: 52
<212> TYPE: PRT
<213> ORGANISM: Canis familiaris

<400> SEQUENCE: 5

```
Tyr Arg Gln Ser Met Asn Asn Phe Gln Gly Pro Arg Ser Phe Gly Cys
  1               5                  10                  15

Arg Phe Gly Thr Cys Thr Val Gln Lys Leu Ala His Gln Ile Tyr Gln
             20                  25                  30

Phe Thr Asp Lys Asp Lys Asp Gly Val Ala Pro Arg Ser Lys Ile Ser
         35                  40                  45

Pro Gln Gly Tyr
     50
```

<210> SEQ ID NO 6
<211> LENGTH: 1432
<212> TYPE: DNA
<213> ORGANISM: Canis familiaris

<400> SEQUENCE: 6

```
ggttttgcca gcaccagagc gacgtctcag accttctcct cccggatctt ggcagatcac     60
cccctcagca gggtctgcgc atcgccgcca gcatgaagct ggttcccgtc gccctcttat    120
acctgggctc cctcgccttc ttgggcgcgg acaccgcacg gctagacgtg gcgtcagagt    180
tccgaaagaa gtggaataaa tgggctgtaa gtcgtggaaa gagggaactt cgagtgtcca    240
gcagctatcc caccgggctc gctgaagtga aggcccgggcc ggcccagact cttattcgga    300
cccaggacgt gaagggcgcc tctcgcaacc cccagaccag cggtccggac gccgccgca    360 tccgagtcaa acgctaccgc cagagtatga acaatttcca gggcccgcgg agcttcggct    420
gccgcttcgg aacgtgcacg gtgcagaaac tggcgcacca gatctaccag ttcacagaca    480
aggacaagga cggcgtcgcc cccaggagca agattagccc tcagggctac ggccgccggc    540
```

-continued

| | | | | |
|---|---|---|---|---|
| gccggcgctc | cctgcccgag | cccggccttc | gccggactct | gttgttcccg | gagccacggc | 600 |
| caggcggggc | tccggccccc | cgggcgcatc | aggtgctcgc | caacctcctt | aagatgtagg | 660 |
| cgcctgtggc | agcagcgaac | tggcgcgcgt | gtgcatcccg | ctggcttccc | cctgggcgga | 720 |
| gggcttcccc | gagccgagcc | cctctgccga | tggaagtcgg | gcagagaccg | ggattccggg | 780 |
| aggcaccgtc | ccgcggccag | ccctggcttt | gcgcgagccc | cttctcctcg | gaggcacgga | 840 |
| tccctctgtc | ccaagccggc | ccaggtgtcc | cgtggggggc | agaggaatgc | aagggaggcc | 900 |
| tgccaggctc | acggagagga | ttaactgaga | attaaatgag | aattaaatgc | ttgagaccct | 960 |
| cccccctccc | ccccccaggga | cagggggtctg | agtcactgcc | gtgcctgccc | acaaactgat | 1020 |
| ttctcacggg | gtgtcacccc | accggggcgc | aagcctcact | attacttgaa | ctttccaaaa | 1080 |
| cctagagagg | aaaagtgcaa | tgcgtgttgt | atatacagag | gtaactatca | atatttaagt | 1140 |
| tcgttgctgt | cagaagattt | tttttgtaac | ttcaaatata | gagatatttt | tgtacgttat | 1200 |
| atattgtatt | aagggcattt | aaaaaccatt | gcattgtccc | cctccccact | tattttaata | 1260 |
| cgtgaatgtc | tcagcgaggt | gtaacgttgt | ttttgctgca | gagtgtgtga | gtgtgcgtga | 1320 |
| gagacttatt | acctcttgtg | gaagaaggaa | caccgtgtct | ctgcattatc | tatttacata | 1380 |
| aaatgggtga | tatgcgaaaa | tagcaaatca | ataataaacg | gtctcgatgc | tg | 1432 |

<210> SEQ ID NO 7
<211> LENGTH: 52
<212> TYPE: PRT
<213> ORGANISM: Bos taurus

<400> SEQUENCE: 7

Tyr Arg Gln Ser Leu Asn Asn Phe Gln Gly Leu Arg Ser Phe Gly Cys
1               5                   10                  15

Arg Phe Gly Thr Cys Thr Val Gln Lys Leu Ala His Gln Ile Tyr His
            20                  25                  30

Phe Thr Asp Lys Asp Lys Asp Gly Ser Ala Pro Arg Ser Lys Ile Ser
        35                  40                  45

Pro Gln Gly Tyr
    50

<210> SEQ ID NO 8
<211> LENGTH: 1439
<212> TYPE: DNA
<213> ORGANISM: Bos taurus

<400> SEQUENCE: 8

| | | | | |
|---|---|---|---|---|
| cgggaaacag | ctcgaacctt | ctcacttttg | gcttctcact | gcagcttcga | cgtcggggtt | 60 |
| ttgccactgc | cagaacgccg | tctcagactt | aatactccaa | agaattttgg | cagatcaccc | 120 |
| cctcagcagg | gtctgcgcat | cgccgccggg | atgaagctgg | ttcccgtcgc | cctcctgtac | 180 |
| ctggggtcgc | tcgccttcct | aggcgtgac | acggcacggc | tcgacgtggc | ggcagagttc | 240 |
| cgaaagaaat | ggaataagtg | ggctctaagt | cgtggaaaaa | gagaacttcg | cgagtccagt | 300 |
| agctacccca | ccgggctcgc | cgacgtgaag | gccgggcctg | tccagactct | tattcggccc | 360 |
| caggatgtaa | agggcgcctc | tcgaagccct | caggccagca | gtcctgacgc | agcccgcatc | 420 |
| cgagtcaagc | gctaccgcca | gagtttgaac | aacttccagg | gcctgcggag | cttcggttgt | 480 |
| cgcttcggga | catgcacggt | gcagaagttg | gcgcatcaga | tctaccattt | cacggacaag | 540 |
| gacaaggacg | gatccgcccc | caggagcaag | atcagccccc | agggctacgg | ccgtcggcgc | 600 |
| cgacgttcac | tgcctgaggc | cggcttgggt | cggactctat | tacagcctcc | agagccaaag | 660 |

```
ctgcgagggg ccccggactc ccgggtgcat caagtacttg ccaccctcag gatttaggcg      720
cctgggcagc agcgaacagt cgcgcacgca tctcgccggc acctcttcgg gcgggagggc      780
ttccgcgagc cgagcccctc actcagccta tgggcccggg ctgagaacag ccctgagaga      840
ccgagagtcc aggaggcacc gtccggcagc agcgagcac tggctttgca ggaacccgtc       900
ctcctcggag gggaggcagt gttctcttca ctctaattgg ggccaggtgc agtttctcct      960
ctccgtgagc ctggcagacg ctcacggaga ggagaaactg cgaaataaat gatgagaccc     1020 tcagggcaa gggtctgagc cactgccgtg cccgcccaca aactgattcc tgatgggggt     1080
gtcaccccac cggggtgcaa gcctcactat tacttgaact ttccgaaacc tagagaggaa     1140
aagtgcaatg agtgttgtat atacagagat aattatcaat atttaaattt gttgttgtca     1200 agatttttt tgtaacttca aatatagaga tattttgta cgttatatat tgtattaagg      1260 gcatttaaa gcaattgtat tgttcccctc ccctctattt taataagtga atgtctcagc      1320
gagatgcaac gttgtttgct gcgtggaatg tgagagtgtg tgcgtgaaag agatgagttg     1380
cctcttgtgg aagaagaaaa caccgtgtct gtataatcta tttacataaa gtgggccgg     1439
```

<210> SEQ ID NO 9
<211> LENGTH: 50
<212> TYPE: PRT
<213> ORGANISM: Rattus norvegicus

<400> SEQUENCE: 9

Tyr Arg Gln Ser Met Asn Gln Gly Ser Arg Ser Thr Gly Cys Arg Phe
  1               5                  10                  15

Gly Thr Cys Thr Met Gln Lys Leu Ala His Gln Ile Tyr Gln Phe Thr
             20                  25                  30

Asp Lys Asp Lys Asp Gly Met Ala Pro Arg Asn Lys Ile Ser Pro Gln
         35                  40                  45

Gly Tyr
     50

<210> SEQ ID NO 10
<211> LENGTH: 1376
<212> TYPE: DNA
<213> ORGANISM: Rattus norvegicus

<400> SEQUENCE: 10

```
tccagccttt accgctcctg gtttctcggc ttctcatcgc agtcagtctt ggactttgcg       60
ggttttgccg ctgtcagaag gacgtctcgg actttctgct tcaagtgctt gacaactcac      120
cctttcagca gggtatcgga gcatcgctac agaatgaagc tggtttccat cgccctgatg      180
ttattgggtt cgctcgccgt tctcggcgcg gacaccgcac ggctcgacac ttcctcgcag      240
ttccgaaaga gtggaataa gtgggcgcta agtcgtggga gagggaact acaagcgtcc       300 agcagctacc ctacggggct cgttgatgag aagacagtcc cgaccagac tcttgggctc       360 caggacaagc agagcacgtc tagcaccca aagccagca ctcagagcac agcccacatt       420
cgagtcaaac gctaccgcca gagcatgaac caggggtccc gcagcactgg atgccgcttt      480
gggacctgca caatgcagaa actggctcac cagatctacc agtttacaga caaagacaag     540
gacggcatgg ccccagaaa caagatcagc cctcaaggct atggccgccg gcgccggcgt      600
tccctgccag aggtcctccg agcccggact gtggagtcct cccaggagca gacacactca     660
gctccagcct ccccggcgca ccaagacatc tccagagtct ctaggttata ggtgcgggtg     720
```

```
gcagcattga acagtcgggc gagtatccca ttggcgcctg cggaatcaga gagcttcgca    780
ccctgagcgg actgagacaa tcttgcagag atctgcctgg ctgccccctag gggaggcaga   840 ggaacccaag atcaagccag gctcacgtca gaaaccgaga attacaggct gatactctct    900
ccgggcaggg gtctgagcca ctgccttgcc cgctcataaa ctggttttct cacggggcat    960
acggctcatt acttacttga actttccaaa acctagcgag gaaaagtgca atgcttgtta    1020
tacagccaaa ggtaactatc atatttaagt ttgttgatgt caagaggttt ttttttttgt    1080
aacttcaaat atatagaaat attttgtac gttatatatt gtattaaggg cattttaaag     1140
cgattatatt gtcaccttcc cctatttaa gaagtgaatg tctcagcaag gtgtaaggtt     1200
gtttggttcc gtgtgtgtgt gtgtgtgtgt gtgtgtgtgt gtgtgtgtgt gtgtgtaagg    1260
tggagagcgc ctgattaccg cctgtggatg aagaaaaaac attgtgtctt ctataatcta    1320
tttacataaa atatgtgatc tgggaaaaag caaaccaata aactgtctca atgctg         1376

<210> SEQ ID NO 11
<211> LENGTH: 50
<212> TYPE: PRT
<213> ORGANISM: Mus musculus

<400> SEQUENCE: 11

Tyr Arg Gln Ser Met Asn Gln Gly Ser Arg Ser Asn Gly Cys Arg Phe
 1               5                  10                  15

Gly Thr Cys Thr Phe Gln Lys Leu Ala His Gln Ile Tyr Gln Leu Thr
                20                  25                  30

Asp Lys Asp Lys Asp Gly Met Ala Pro Arg Asn Lys Ile Ser Pro Gln
            35                  40                  45

Gly Tyr
    50

<210> SEQ ID NO 12
<211> LENGTH: 1381
<212> TYPE: DNA
<213> ORGANISM: Mus musculus

<400> SEQUENCE: 12
cttggtgaca ctagacagag caactccagc gttaccgctc ccgctcctgg tttctcggct    60
tctcatcgca gtcaatcttg gactttgggg ttttgctact gtcagaagga cttctttctg    120
cttcaagtgc ttgacaacgc acccctttat cagggtatca gagcatcgcc acagaatgaa    180
gctggtttcc atcaccctga tgttattggg ttcactcgct ttcctaggcg cggacactgc    240
agggccagat actccttcgc agttccgaaa gaagtggaat aagtgggcgc taagtcgtgg    300
gaagagggaa ctacaagcat ccagcagcta ccctacggga ctcgctgatg agacgacagt    360
tcctacccag actcttgatc cattcctgga cgagcagaac acaactggcc cctacaagc     420 cagcaatcag agcgaagccc acattcgtgt caaacgctac cgccagagca tgaaccaggg    480
ttcccgcagc aatggatgcc gcttcgggac ctgcacattt cagaaattgg cccaccagat    540
ctaccagcta acagacaaag acaaggacgg catggctccc agaaacaaga tcagccctca    600
aggctatggc cgccggcgcc ggcgttccct gctggaggtc ctccggtccc ggactgtgga    660
gtcctcccag gagcagacac acacagcccc aggcccctgg gcgcacatct ccagactctt    720
taggatatag gtgcgggtga cagcattgaa cagtcgggcg agtatcccgt tggcgcctgc    780
ggaatcagag aacttcgcac cggggcggac tgagacaatc ctgcagagat ctgcctggct    840
gcccctaggg gaggcagagg aacccaagac caagccaggc tcatgccaga aaccgagact    900
```

```
tacaggctga tactctccgg gcagggtct gagccactgc cttgcccgct cataaactgg    960
tttctcacgg ggcataagcc tcattactac ttgaactttc caaaacctag cgaggaacgt   1020
gcaatgcttg ttgtccagcc aaaggtaact atagtattta agtttgttgc tgtcaaggtt   1080 ttttttttg taacttcaaa tatatagaga tattttgta cgttatatat tgtattaagg     1140
gcattttaaa gtgattatat tgtcaccttc ccctatttta agacgtgaat gtctcagcaa   1200
ggtgtaaggt tgtttggttc cgtgtgtgtg tgtgtgtgtg tgtgtgtgtg tgtgtgtgtg   1260
taaggtggag agcgcctgat tatcgcctgt ggatgaagaa aaaacattgt gtttcctata   1320
atctatttac ataaaatatg tgatctggga aaaagcaaac caataaactg tctcaatgct   1380
g                                                                  1381
```

METHOD FOR PREVENTION OR TREATMENT OF INTRACTABLE INFLAMMATORY BOWEL DISEASE

CROSS-REFERENCE TO RELATED APPLICATIONS

This application is a national stage application under 35 U.S.C. §371 of PCT/JP2012/051010, filed Jan. 12, 2012, which claims benefit of U.S. provisional Appl. No. 61/431,975, filed Jan. 12, 2011, which is incorporated herein by reference.

SEQUENCE LISTING

The Sequence Listing associated with this application is filed in electronic format via EFS-Web and hereby is incorporated by reference into the specification. The name of the text file containing the Sequence Listing is Replacement_Seq_List_119244-00060_ST25.txt. The size of the text file is 16.4 KB, and the text file was created on Jul. 10, 2013.

TECHNICAL FIELD

The present invention relates to a method for preventing or treating intractable inflammatory bowel diseases, particularly an inflammatory bowel disease for which the use of a steroid preparation, an immunosuppressant, or a biological product is difficult or insufficiently effective and a steroid-resistant or steroid-dependent inflammatory bowel disease, by administering adrenomedullin.

BACKGROUND ART

Ulcerative colitis and Crohn's disease are collectively called inflammatory bowel disease (IBD), and are both unexplained refractory diseases having a predilection for the juvenile to adolescent people and repeating recrudescence. In Japan, ulcerative colitis and Crohn's disease have been listed as diseases for specified disease treatment research since 1975 (October, Showa 50) and 1976 (October, Showa 51), respectively. The number of patients with these diseases tends to increase in Japan, and among them, that of those with ulcerative colitis is more than 100,000. A peak of age at onset is seen between the late-10s and the early-30s; however, onset in advanced age has also increased. Because more common in young people, the diseases greatly interfere with social life such as academic life, working, and marriage; the goal of treatment of the diseases is to control the disease state to enable the continuance of normal social life, under present circumstances in which they are of unknown cause and has no radical cure.

The disease state of ulcerative colitis is classified according to the diseased area and the course and severity thereof; it is classified into "proctitis type", "left-side colitis type", and "whole colitis type" by area and into "fulminant", "severe", "moderate", and "mild" depending on clinical manifestation by severity. On the other hand, Crohn's disease can occur all over the alimentary tract; thus, its symptom is diverse and these symptoms are sometimes intermittently seen. It is classified by lesion area into "small bowel type", whose lesions are present only in the small bowel, "large bowel type", whose lesions are present only in the large bowel, and "small-bowel/large-bowel type", whose lesions are present in both of these areas. It may be classified by lesion type into "inflammation type", "narrowing type", and "perforation type"; the latter shows more intractable nature and is clinically problematical. The severe case and the mild case greatly differ in symptoms; the symptoms are intense in an active stage (advanced stage) during which inflammation is intense, and the symptoms abate in a remission stage during which the inflammation abates. However, the narrowing, perforation, and fistulae cannot be restored, and the symptoms do not disappear in the remission stage. In addition, there are relative diseases, such as non-specific multiple small-bowel ulcer and bowel Behcet's disease, which not infrequently show intractable nature.

In Japan, both ulcerative colitis and Crohn's disease are treated according to guidelines prepared by a study group of the Ministry of Health, Labour and Welfare. Specifically, systemic administration/local administration of a steroid preparation, blood component removal therapy, immunosuppressant therapy, biological product therapy, and the like are performed on the basis of an aminosalicylic acid preparation and nutrition therapy. Steroid therapy is effective for the remission induction treatment of an inflammatory bowel disease; however, side effects due to long-term steroid therapy and their attendant reduction in QOL are seen as a problem. Although steroid therapy should be reduced to minimum necessary, cases exist in which a sufficient effect is not obtained by another treatment method (an aminosalicylic acid preparation). Particularly, elderly people are at risk of having complication of severe infection associated with the use of a steroid drug, an immunosuppressant, or a biological product; the use of these drugs is restricted.

In addition, for ulcerative colitis, "steroid-resistant cases" not responsive to steroid therapy exerting the strongest treatment effect or "steroid-dependent cases" in which the effect of steroid therapy is obtained but recrudescence occurs during the tapering of steroid exist in no small numbers, and have become problematical as "intractable" ulcerative colitis. Adverse events due to long-term use of steroid have become a problem; thus, it is important how remission can be maintained by treatment not relying on steroid. Patients with intractable inflammatory bowel disease sometimes become relative candidates for surgery since the excessive administration of steroid or the maintenance of remission is difficult, which markedly impairs QOL, and existing steroid therapy and immunosuppressant therapy have limitations; thus, a new treatment strategy is necessary. For Crohn's disease, a high remission-inducing effect of a biological product (an anti-TNF-α agent) has been observed in recent years; however, as for a long-term remission-maintaining effect, it has turned out that the agent alone cannot maintain remission in about half of patients. Although the effect of a combination of an immunosuppressant therewith has also been studied, reports of occurrence of malignant lymphoma have been increasing; thus, there is need for the development of a new treatment strategy other than a biological product and an immunosuppressant. Unexplained relative diseases having difficulties in treatment also exist, such as non-specific multiple small-bowel ulcer and bowel Behcet's disease; however, treatment methods for these diseases have not been established.

CITATION LIST

Patent Literature

Patent Literature 1: JP Patent Publication (Kokai) No. 2006-290777A

Non Patent Literature

Non Patent Literature 1: Ashizuka S., Inagaki-Ohara K., Kuwasako K., Kato J., Inatsu H., Kitamura K.; Adrenomedullin treatment reduces intestinal inflammation and maintains epithelial barrier function in mice administered dextran sulphate sodium., Microbiol Immunol. 2009 October; 53(10): 573-81.

Non Patent Literature 2: Ashizuka S., Ishikawa N., Kato J., Yamaga J., Inatsu H., Eto T., Kitamura K.; Effect of adrenomedullin administration on acetic acid-induced colitis in rats., Peptides. 2005 December; 26(12): 2610-5. Epub 2005 Jun. 23.

Non Patent Literature 3: Gonzales-Rey E., Fernandez-Martin A., Chorny A., et al.; Therapeutic effect of urocortin and adrenomedullin in a murine model of Crohn's disease., Gut 2006; 55: 824-832.

Non Patent Literature 4: Talero E., Sánchez-Fidalgo S., de la Lastra C A, et al.; Acute and chronic responses associated with adrenomedullin administration in experimental colitis., Peptides. 2008; 29: 2001-12.

SUMMARY OF INVENTION

Technical Problem

The possibility of inducing remission of an inflammatory bowel disease is expected by performing 1) steroid therapy; 2) immunosuppressant therapy (including biological product therapy); or 3) operative therapy. However, for the respective therapies, concerns exist about 1) side effects due to the long-term administration of steroid, such as osteoporosis, hypertension, diabetes, glaucoma, and infection; 2) side effects associated with an immunosuppressant, especially susceptibility to infection (ease of infection) and digestive symptoms such as diarrhea; and 3) risks and disadvantages such as large invasion (body burden) of operative therapy and frequent occurrence of diarrhea due to colostomy and after colostomy withdrawal.

Adrenomedullin has hitherto proved to reduce organ damage in a systemic inflammatory response syndrome (SIRS) animal model, which demonstrates that the adrenomedullin exerts an anti-inflammatory action. In addition, adrenomedullin (enema and intraperitoneal administration) has proved to have curative properties against inflammation of the large bowel in large bowel ulcer model rats and colitis model mice, and the suppression of production of an inflammatory cytokine is considered to be involved in the mechanism of the properties. There are also a plurality of reports that adrenomedullin also has curative properties against inflammation in gastric mucosal damage model rats, and the adrenomedullin probably also has curative properties against intestinal mucosal damage.

However, no treatment effect of adrenomedullin is known on a steroid-resistant or steroid-dependent inflammatory bowel disease. No effective method for administering adrenomedullin is also known for these diseases.

Thus, an object of the present invention is to provide methods for preventing or treating a steroid-resistant or steroid-dependent inflammatory bowel disease using adrenomedullin.

Another object of the present invention is to provide a method for preventing or treating an inflammatory bowel disease for which the use of a steroid preparation, an immunosuppressant, or a biological product is difficult or insufficiently effective, in a patient with the inflammatory bowel disease by using adrenomedullin.

Solution to Problem

The present invention includes the following inventions.
(1) A method for preventing or treating an inflammatory bowel disease for which the use of a steroid preparation, an immunosuppressant, or a biological product is difficult or insufficiently effective, in a patient in need of the prevention or treatment of the inflammatory bowel disease, comprising administering an effective amount of adrenomedullin, a modified product thereof having an activity of suppressing inflammation, or a salt of the adrenomedullin or the modified product, having an activity of suppressing inflammation, to the patient.

(2) A method for preventing or treating a steroid-resistant or steroid-dependent inflammatory bowel disease in a patient in need of the prevention or treatment of the inflammatory bowel disease, comprising administering an effective amount of adrenomedullin, a modified product thereof having an activity of suppressing steroid-resistant or steroid-dependent inflammation, or a salt of the adrenomedullin or the modified product, having an activity of suppressing steroid-resistant or steroid-dependent inflammation, to the patient.

(3) The prevention or treatment method according to (1) or (2), wherein the adrenomedullin or the modified product is a peptide of any of the following (i) to (vi):
  (i) a peptide consisting of the amino acid sequence of adrenomedullin;
  (ii) a peptide consisting of the amino acid sequence of adrenomedullin whose two intramolecular Cys are disulfide bonded;
  (iii) a peptide of (ii) in which the disulfide bond is substituted with —$CH_2$—$CH_2$— bond;
  (iv) a peptide of any of (i) to (iii) having deletion, substitution, or addition of 1 to 15 amino acids and having an activity of suppressing steroid-resistant or steroid-dependent inflammation;
  (v) a peptide of any of (i) to (iv) whose C-terminus is amidated; and
  (vi) a peptide of any of (i) to (iv) having addition of Gly at the C-terminus.

(4) The prevention or treatment method according to any of (1) to (3), wherein the adrenomedullin or the modified product is a peptide of any of the following (a) to (j):
  (a) a peptide consisting of the amino acid sequence of SEQ ID NO: 1, or a peptide consisting of the amino acid sequence of SEQ ID NO: 1 in which Cys at position 16 and Cys at position 21 are disulfide bonded;
  (b) a peptide consisting of the amino acid sequence of SEQ ID NO: 3, or a peptide consisting of the amino acid sequence of SEQ ID NO: 3 in which Cys at position 16 and Cys at position 21 are disulfide bonded;
  (c) a peptide consisting of the amino acid sequence of SEQ ID NO: 5, or a peptide consisting of the amino acid sequence of SEQ ID NO: 5 in which Cys at position 16 and Cys at position 21 are disulfide bonded;
  (d) a peptide consisting of the amino acid sequence of SEQ ID NO: 7, or a peptide consisting of the amino acid sequence of SEQ ID NO: 7 in which Cys at position 16 and Cys at position 21 are disulfide bonded;
  (e) a peptide consisting of the amino acid sequence of SEQ ID NO: 9, or a peptide consisting of the amino acid sequence of SEQ ID NO: 9 in which Cys at position 14 and Cys at position 19 are disulfide bonded;
  (f) a peptide consisting of the amino acid sequence of SEQ ID NO: 11, or a peptide consisting of the amino acid sequence of SEQ ID NO: 11 in which Cys at position 14 and Cys at position 19 are disulfide bonded;
  (g) a peptide of any of (a) to (f) in which the disulfide bond is substituted with —$CH_2$—$CH_2$— bond;

(h) a peptide of any of (a) to (g) having deletion, substitution, or addition of 1 to 15 amino acids and having an activity of suppressing steroid-resistant or steroid-dependent inflammation;

(i) a peptide of any of (a) to (h) whose C-terminus is amidated; and (j) a peptide of any of (a) to (h) having addition of Gly at the C-terminus.

(5) The prevention or treatment method according to any of (1) to (4), wherein the adrenomedullin, the modified product, or the salt is intravenously administered continuously.

(6) The prevention or treatment method according to (5), wherein the intravenous administration is continuously performed at a rate of 1.0 to 2.0 pmol/kg body weight/min.

(7) The prevention or treatment method according to (5) or (6), wherein the intravenous administration is continuously performed for 6 to 10 hours per day.

(8) The prevention or treatment method according to any of (5) to (7), wherein the intravenous administration is performed for 7 to 21 days.

The present invention also includes the following inventions.

An agent for preventing or treating a steroid-resistant or steroid-dependent inflammatory bowel disease, comprising adrenomedullin, a modified product thereof having an activity of suppressing steroid-resistant or steroid-dependent inflammation, or a salt thereof having an activity of suppressing steroid-resistant or steroid-dependent inflammation, as an active ingredient.

An agent for preventing or treating an inflammatory bowel disease for which the use of a steroid preparation, an immunosuppressant, or a biological product is difficult or insufficiently effective, comprising adrenomedullin, a modified product thereof having an activity of suppressing inflammation, or a salt thereof having an activity of suppressing inflammation, as an active ingredient.

Adrenomedullin, a modified product thereof having an activity of suppressing inflammation, or a salt of the adrenomedullin or the modified product, having an activity of suppressing inflammation, for use in the prevention or treatment of an inflammatory bowel disease for which the use of a steroid preparation, an immunosuppressant, or a biological product is difficult or insufficiently effective.

Use of adrenomedullin, a modified product thereof having an activity of suppressing inflammation, or a salt of the adrenomedullin or the modified product, having an activity of suppressing inflammation, in the manufacture of a medicament for use in the prevention or treatment of an inflammatory bowel disease for which the use of a steroid preparation, an immunosuppressant, or a biological product is difficult or insufficiently effective.

The above prevention or treatment is preferably the prevention or treatment of an inflammatory bowel disease by continuously intravenously administering adrenomedullin, a modified product thereof having an activity of suppressing inflammation, or a salt of the adrenomedullin or the modified product, having an activity of suppressing inflammation, to a patient.

The intravenous administration is preferably continuously performed at a rate of 1.0 to 2.0 pmol/kg body weight/min.

The intravenous administration is preferably continuously performed for 6 to 10 hours per day.

The intravenous administration is preferably performed for 7 to 21 days.

The present specification encompasses the contents of the specification and/or drawings of U.S. provisional application No. 61/431,975 on which the priority of the present application is based.

Advantageous Effects of Invention

According to the present invention, a steroid-resistant or steroid-dependent inflammatory bowel disease can be prevented or treated.

An inflammatory bowel disease for which the use of a steroid preparation, an immunosuppressant, or a biological product is difficult or insufficiently effective can be prevented or treated in a patient with the inflammatory bowel disease.

BRIEF DESCRIPTION OF DRAWINGS

The patent or application file contains at least one drawing executed in color. Copies of this patent or patent application publication with color drawings will be provided by the Office upon request and payment of the necessary fee.

FIG. 1 is a pair of photographs showing endoscopic findings at the time of admission of a patient in Examples. Strong edema, pus, and multiple ulcers were observed (moderate<severe). Thereafter, steroid powerful intravenous injection therapy+leucocyte apheresis therapy (LCAP) was started.

FIG. 3 is a pair of photographs showing endoscopic findings at 18 days after administering the antiviral agent. Dig deep ulcer was further expanded (severe). Thereafter, adrenomedullin (AM) was continuously administered.

DESCRIPTION OF EMBODIMENTS

Figure 2:
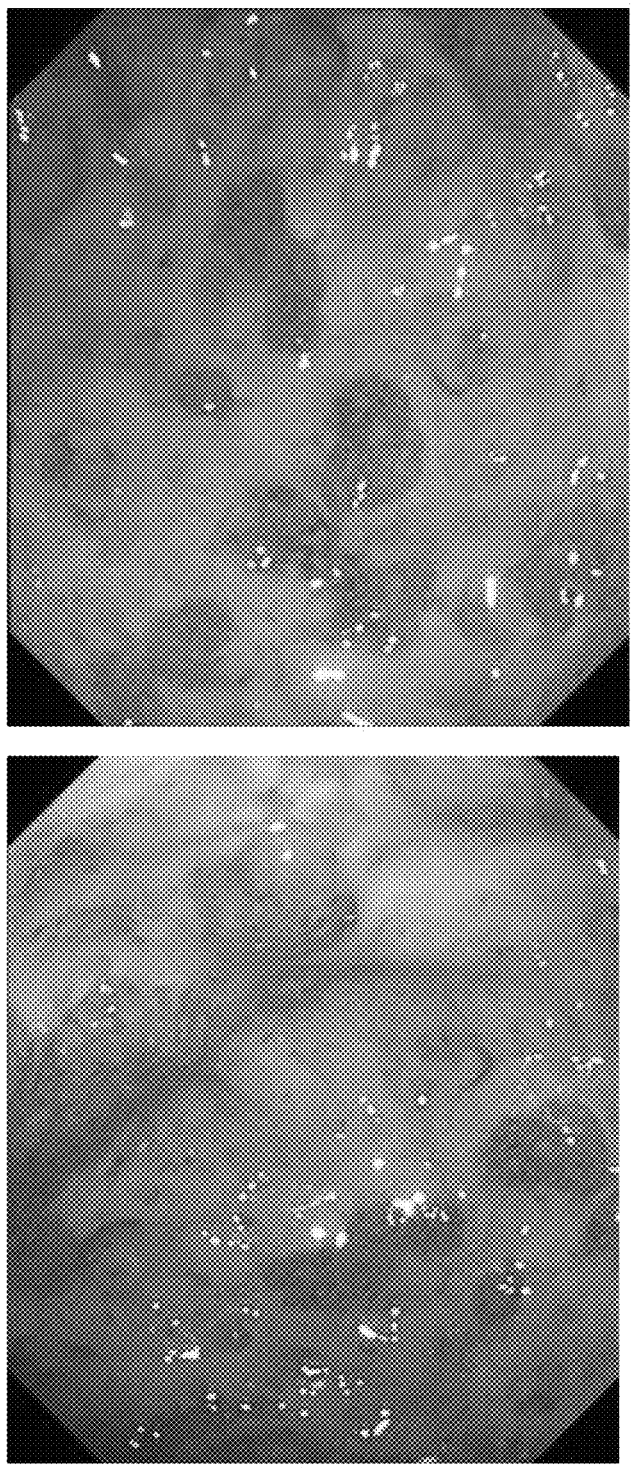
FIG. 2 is a pair of photographs showing endoscopic findings at 10 days after starting steroid powerful intravenous injection therapy+leucocyte apheresis therapy. Dig deep ulcer was enlarged (severe, cytomegalovirus-positive). Thereafter, an antiviral agent was administered.

The present invention will be described below in detail.

The present invention relates to a method for preventing or treating a steroid-resistant or steroid-dependent inflammatory bowel disease by administering an effective amount of adrenomedullin, a modified product thereof having an activity of suppressing steroid-resistant or steroid-dependent inflammation, or a salt thereof having an activity of suppressing steroid-resistant or steroid-dependent inflammation, to a patient.

The present invention also relates to a method for preventing or treating an inflammatory bowel disease by administering an effective amount of adrenomedullin, a modified product thereof having an activity of suppressing inflammation, or a salt thereof having an activity of suppressing inflammation to a patient with the inflammatory bowel disease for which the use of a steroid preparation, an immunosuppressant, or a biological product is difficult or insufficiently effective.

1. Patient

Examples of the intended patients of the present invention can include patients suffering from an inflammatory bowel disease (including relative diseases for the present invention).

In addition, examples of the intended patients of the present invention can also include the following patients:

(I) a patient with an inflammatory bowel disease for which the use of a steroid preparation, an immunosuppressant, or a biological product is difficult or insufficiently effective;

(II) a patient with an inflammatory bowel disease, determined to be steroid-resistant; or (III) a patient with an inflammatory bowel disease, determined to be steroid-dependent.

The patients particularly intended according to the present invention are patients suffering from a steroid-resistant or steroid-dependent inflammatory bowel disease (for example, ulcerative colitis, Crohn's disease, or bowel Behcet's disease), and the most intended patients are patients suffering from steroid-resistant or steroid-dependent ulcerative colitis. The intended patients according to the present invention may also be patients suffering from an inflammatory bowel disease for which the use of a steroid preparation, an immunosuppressant, or a biological product is difficult or insufficiently effective. Examples of the patients with an inflammatory bowel disease for which the use of a steroid preparation, an immunosuppressant, or a biological product is difficult or insufficiently effective include patients in whom the administration of these preparations is unacceptable in prevention or treatment (for example, patients with contraindications to a steroid preparation, an immunosuppressant or a biological product, or patients to whom the agents cannot be administered because of side effects or a risk thereof), patients in whom the effect of prevention or treatment by the administration of the agent cannot be expected sufficiently, and patients not desiring prevention or treatment by the administration of the agent. The patients in whom the use of a steroid preparation is difficult or insufficiently effective include patients suffering from a steroid-resistant or steroid-dependent inflammatory bowel disease.

It has previously been described that among prevention or treatment methods for an inflammatory bowel disease is steroid administration, immunosuppressant administration (including biological product administration), or surgery. The intended patients according to the present invention further include (IV) patients suffering from an inflammatory bowel disease in which the implementation of these existing prevention or treatment methods is difficult or insufficiently effective.

Examples of the types of the patients can include humans and other mammals (for example, mice, rats, guinea pigs, rabbits, chickens, sheep, pigs, cows, cats, dogs, monkeys, hamadryas, and chimpanzees). The intended patients according to the present invention are preferably humans.

2. Active Ingredient

The active ingredients used in the present invention are adrenomedullin, modified products thereof having an activity of suppressing steroid-resistant or steroid-dependent inflammation (inflammation in the bowel), or salts thereof having an activity of suppressing steroid-resistant or steroid-dependent inflammation (inflammation in the bowel). When the intended patient is a patient suffering from an inflammatory bowel disease for which the use of a steroid preparation, an immunosuppressant, or a biological product is difficult or insufficiently effective, the active ingredient may be adrenomedullin, a modified product thereof having an activity of suppressing inflammation (inflammation in the bowel), or a salt thereof having an activity of suppressing inflammation (inflammation in the bowel).

The adrenomedullin used in the present invention may be that derived from humans or other warm-blooded animals (for example, pigs, dogs, cows, rats, or mice). Modified products of adrenomedullin, having an activity of suppressing inflammation or an activity of suppressing steroid-resistant or steroid-dependent inflammation may also be used in the present invention.

Examples of the adrenomedullin or a modified product thereof used in the present invention can include:

(i) a peptide consisting of the amino acid sequence of adrenomedullin;

(ii) a peptide consisting of the amino acid sequence of adrenomedullin whose two intramolecular Cys are disulfide bonded;

(iii) a peptide of (ii) in which the disulfide bond is substituted with —$CH_2$—$CH_2$— bond;

(iv) a peptide of any of (i) to (iii) having deletion, substitution, or addition of 1 or a plurality of, for example, 1 or several, specifically 1 to 15, preferably 1 to 12, more preferably 1 to 10, more preferably 1 to 8, more preferably 1 to 5, most preferably 1 to 3 amino acids and having an activity of suppressing inflammation or an activity of suppressing steroid-resistant or steroid-dependent inflammation;

(v) a peptide of any of (i) to (iv) whose C-terminus is amidated; and (vi) a peptide of any of (i) to (iv) having addition of Gly at the C-terminus.

The "peptide consisting of the amino acid sequence of adrenomedullin" of (i) above means a peptide which is composed only of amino acids constituting adrenomedullin and in which intramolecular disulfide bond, C-terminal amide, and the like are not formed.

Among the peptides of (i) to (vi) above, the peptide which consists of the amino acid sequence of adrenomedullin and in which two intramolecular Cys are disulfide bonded and the C-terminus is amidated, included in (v) is adrenomedullin in the present applied invention, and other peptides are to be referred to as modified products of adrenomedullin.

Examples of the peptides belonging to (iv) above can include peptides having deletion of the amino acids at positions 1 to 15, positions 1 to 12, positions 1 to 10, positions 1 to 8, positions 1 to 5, or positions 1 to 3 from the N-terminus in the amino acid sequence. Peptides having further deletion, substitution, or addition of 1 or several (for example, 1 to 5, 1 to 3, or 1 or 2) amino acids in the above peptides and having an activity of suppressing inflammation or an activity of suppressing steroid-resistant or steroid-dependent inflammation can also be used in the present invention.

The "amidation of the C-terminus" refers to one of modification reactions of a peptide and means that the COOH group of the C-terminal amino acid of the peptide is converted into the form of $CONH_2$. Many bioactive peptides active in vivo are first biosynthesized in the form of a precursor protein having a larger molecular weight, which is then matured by being subjected to a modification reaction such as C-terminal amidation during intracellular migration. The amidation is effected by the action of a C-terminal amidation enzyme on the precursor protein. In the precursor protein, a Gly residue is always present at the side of the C-terminus which is a residue to be amidated, and for example, a sequence of a pair of basic amino acids, such as Lys-Arg or Arg-Arg, is often further added to the side of the C-terminus (Mizuno, Seikagaku (Biochemistry), vol. 61, no. 12, pp. 1435-1461 (1989)).

The disulfide bond can be formed, for example, by air oxidation or oxidation using an appropriate oxidizing agent. The substitution of the disulfide bond into —CH$_2$—CH$_2$— can be performed by a well-known method (O. Kelleret et al., Helv. Chim. Acta (1974) 57: 1253). The substitution of a disulfide bond with —CH$_2$—CH$_2$— bond generally avoids the cleavage of the disulfide bond to stabilize a protein.

Specific examples of the adrenomedullin or a modified product thereof used in the present invention can include:

(a) a peptide consisting of the amino acid sequence of SEQ ID NO: 1, or a peptide which consists of the amino acid sequence of SEQ ID NO: 1 and in which Cys at position 16 and Cys at position 21 are disulfide bonded;

(b) a peptide consisting of the amino acid sequence of SEQ ID NO: 3, or a peptide which consists of the amino acid sequence of SEQ ID NO: 3 and in which Cys at position 16 and Cys at position 21 are disulfide bonded;

(c) a peptide consisting of the amino acid sequence of SEQ ID NO: 5, or a peptide which consists of the amino acid sequence of SEQ ID NO: 5 and in which Cys at position 16 and Cys at position 21 are disulfide bonded;

(d) a peptide consisting of the amino acid sequence of SEQ ID NO: 7, or a peptide which consists of the amino acid sequence of SEQ ID NO: 7 and in which Cys at position 16 and Cys at position 21 are disulfide bonded;

(e) a peptide consisting of the amino acid sequence of SEQ ID NO: 9, or a peptide which consists of the amino acid sequence of SEQ ID NO: 9 and in which Cys at position 14 and Cys at position 19 are disulfide bonded;

(f) a peptide consisting of the amino acid sequence of SEQ ID NO: 11, or a peptide which consists of the amino acid sequence of SEQ ID NO: 11 and in which Cys at position 14 and Cys at position 19 are disulfide bonded;

(g) a peptide of any of (a) to (f) in which the disulfide bond is substituted with —CH$_2$—CH$_2$— bond;

(h) a peptide of any of (a) to (g) having deletion, substitution, or addition of 1 or a plurality of, for example, 1 or several, specifically 1 to 15, preferably 1 to 12, more preferably 1 to 10, more preferably 1 to 8, more preferably 1 to 5, most preferably 1 to 3 amino acids and having an activity of suppressing inflammation or an activity of suppressing steroid-resistant or steroid-dependent inflammation;

(i) a peptide of any of (a) to (h) whose C-terminus is amidated; and (j) a peptide of any of (a) to (h) having addition of Gly at the C-terminus.

Examples of the peptides belonging to (h) above include peptides having deletion of the amino acids at positions 1 to 15, positions 1 to 12, positions 1 to 10, positions 1 to 8, positions 1 to 5, or positions 1 to 3 in a peptide consisting of the amino acid sequence of SEQ ID NO: 1, 3, 5, 7, 9, or 11 (which may comprise the intramolecular bond shown in each of (a) to (g) above). Among them, preferred are peptides having deletion of the amino acids at positions 1 to 12 in a peptide consisting of the amino acid sequence of SEQ ID NO: 1, 3, 5, or 7 (which may comprise the above intramolecular bond), and peptides having deletion of the amino acids at positions 1 to 10 in a peptide of the amino acid sequence of SEQ ID NO: 9 or 11 (which may comprise the above intramolecular bond). Peptides having further deletion, substitution, or addition of 1 or several (for example, 1 to 5, 1 to 3, or 1 or 2) amino acids in the above peptides and having an activity of suppressing inflammation or an activity of suppressing steroid-resistant or steroid-dependent inflammation can also be used in the present invention.

Examples of modified products of adrenomedullin other than the above, used in the present invention include ones in which some of the amino acid residues constituting a peptide of each of (a) to (j) above are amidated or esterified and which have an activity of suppressing inflammation or an activity of suppressing steroid-resistant or steroid-dependent inflammation. Examples of the esters include ones in which a C-terminal carboxyl group is esterified in each of (a) to (h) and (j).

Adrenomedullin or a modified product thereof may also be provided in the form of a precursor or a prodrug compound capable of being converted into adrenomedullin or the modified product thereof by in vivo metabolism. They may also be provided in the form of hydrates or solvates. Such forms also fall within the scope of the present invention. As an example of the precursor, a peptide consisting of the 1st to 185th amino acid sequence encoded by the nucleic acid sequence of SEQ ID NO: 2 or a peptide consisting of a partial sequence thereof comprising the 95th to 146th amino acids is cited. The peptide of (j) above is probably converted into a mature peptide by the amidation of its C-terminus in vivo after administration; thus, the peptide can also be included in the category of the precursor of adrenomedullin or a modified product thereof.

Salts of adrenomedullin or a modified product thereof having an activity of suppressing inflammation or an activity of suppressing steroid-resistant or steroid-dependent inflammation may also be used in the present invention. The salts may be, for example, any pharmaceutically acceptable salt with a base (for example, an alkali metal) or an acid (an organic acid or an inorganic acid); however, examples thereof include inorganic acid salts, such as hydrochlorides, hydrobromates, hydroiodides, sulfates, nitrates, phosphates, carbonates, hydrogen carbonates, and perchlorates; organic acid salts, such as formats, acetates, trifluoroacetates, propionates, oxalates, glycolates, succinates, lactates, maleates, hydroxymaleates, methylmaleates, fumarates, adipates, tartrates, malates, citrates, benzoates, cinnamates, ascorbates, salicylates, 2-acetoxybenzoates, nicotinates, and isonicotinates; sulfonates, such as methanesulfonates, ethanesulfonates, isethionates, benzenesulfonates, p-toluenesulfonates, and naphthalenesulfonates; alkali metal salts, such as sodium salts and potassium salts; and alkaline-earth metal salts, such as magnesium salts and calcium salts.

Adrenomedullin or a modified product thereof can be produced by a method for purifying any of peptides from tissues or cells of humans or warm-blooded animals, or can be produced according to ordinary peptide synthesis methods. They can also be produced by culturing a transformant containing DNA encoding adrenomedullin.

According to the present invention, adrenomedullin may be provided in the form of a nucleic acid molecule (for example, DNA or RNA) containing a gene sequence encoding adrenomedullin. Thus, the method according to the present invention includes so-called gene therapy. As DNAs encoding adrenomedullin are used, for example, I) DNA containing the nucleotide sequence of SEQ ID NO: 2, 4, 6, 8, 10, or 12, or DNA containing a partial sequence of the nucleotide sequence of SEQ ID NO: 2, 4, 6, 8, 10, or 12, containing a region encoding adrenomedullin in its portion, II) DNA consisting of a nucleotide sequence complementary to the nucleotide sequence of SEQ ID NO: 2, 4, 6, 8, 10, or 12, or mammal-derived DNA which can hybridize to DNA consisting of a nucleotide sequence complementary to a partial sequence of the nucleotide sequence of SEQ ID NO: 2, 4, 6, 8, 10, or 12, containing a region encoding adrenomedullin in its portion, under stringent conditions and which encodes a peptide having an activity of suppressing inflammation or an activity of suppressing steroid-resistant or steroid-dependent inflammation or a precursor thereof, and III) DNA capable of not forming a hybrid with sequences prescribed in I) and II) because of degeneration of genetic codes, but coding a peptide having the same amino acid sequence. The hybridization can be performed according to known methods or methods equivalent thereto. The above stringent conditions are, for example, 42° C., 50% formamide, 4×SSPE (1×SSPE=150 mM NaCl, 10 mM $NaH_2PO_4.H_2O$, 1 mM EDTA pH 7.4), 5×Denhardt's solution, and 0.1% SDS.

The "partial sequence of the nucleotide sequence of SEQ ID NO: 2, 4, 6, 8, 10, or 12, containing a region encoding adrenomedullin in its portion" will be described, citing an example. In SEQ ID NO: 2, the region from T at position 439 to C at position 594 encodes adrenomedullin; thus, a partial sequence of SEQ ID NO: 2 containing the region, for example, the nucleotide sequence from A at position 157 to T at position 711, can be used in the present invention.

When a gene consisting of DNA described in each of I) to III) above is transcribed/translated in vivo, a precursor protein having a molecular weight larger than adrenomedullin generally occurs and then is matured to active adrenomedullin by being subjected to a modification reaction such as C-terminal amidation during intracellular migration.

3. Pharmaceutical Composition

According to the present invention, adrenomedullin, a modified product thereof, or a salt thereof may be used alone, and may be used in the form of a pharmaceutical composition. The pharmaceutical composition may comprise adrenomedullin, a modified product thereof, or a salt thereof, and a pharmaceutically acceptable carrier, a flavoring agent, an excipient, a vehicle, a preservative, a stabilizer, a binder, or the like. The pharmaceutical composition may also comprise other useful ingredients.

Adrenomedullin, a modified product thereof, or a salt thereof may be used in the form of sugar-coated or soluble coating-applied tablets, capsules, elixirs, microcapsules, or the like, if necessary. They may also be used in the form of injections obtained by dissolution or suspension in water or other pharmaceutically acceptable liquids. They can also be directly administered locally.

Examples of the additives which can be added to tablets, capsules, and the like include binders such as gelatin, corn starch, gum tragacanth, and gum arabic, excipients such as crystalline cellulose, swelling agents such as corn starch, gelatin, and alginic acid, lubricants such as magnesium stearate, sweetening agents such as sucrose, lactose, and saccharin, and flavoring agents such as peppermint, Akamono oil, and cherry. Capsules may comprise liquid carriers such as fat and oil in addition to the above materials.

Injections can be prepared by dissolving or suspending an active ingredient in a vehicle such as water for injection. Examples of aqueous liquids for injection include physiological saline and isotonic solutions containing glucose and other adjuvants (D-sorbitol, D-mannitol, sodium chloride, and the like). As a solubilizing agent may be added, for example, an alcohol (ethanol or the like), a polyalcohol (propylene glycol, polyethylene glycol, or the like), or a non-ionic surfactant (polysorbate 80™, HCO-50, or the like). Examples of oily liquids for injection include sesame oil and soybean oil. As a solubilizing agent, for example, benzyl benzoate or benzyl alcohol may be added. A buffer (phosphate buffer, sodium acetate buffer, or the like), a soothing agent (benzalkonium chloride, procaine hydrochloride, or the like), a stabilizer (human serum albumin, polyethylene glycol, or the like), a preserving agent (benzyl alcohol, phenol, or the like), an antioxidant, and the like may also be added. The injection prepared is typically packed in an appropriate ample. The preparation thus obtained is safe and less toxic; thus, it can be administered to humans and mammals (for example, mice, rats, guinea pigs, rabbits, chickens, sheep, pigs, cows, cats, dogs, monkeys, hamadryas, and chimpanzees).

Adrenomedullin, a modified product thereof, or a salt thereof according to the present invention, or a pharmaceutical composition comprising any of them as an active ingredient can be administered alone, or, in some intended patients, can be administered in combination with a steroid preparation, an immunosuppressant, or a biological product for prevention or treatment of an inflammatory bowel disease. A steroid preparation or an immunosuppressant mainly has an inflammation-suppressing effect; however, adrenomedullin, a modified product thereof, or a salt thereof according to the present invention, or a pharmaceutical composition comprising any of them as an active ingredient exerts an inflammation-suppressing effect and a marked mucosa-repairing effect, thereby providing a high prevention or treatment effect.

Depending on the intended patient, they can also be administered in combination with an aminosalicylic acid preparation.

4. Dosage and Administration

According to the present invention, adrenomedullin, a modified product thereof, or a salt thereof is administered in an effective amount to a patient. The "effective amount" means any dosage capable of preventing or treating a steroid-resistant or steroid-dependent inflammatory bowel disease in a patient suffering from the steroid-resistant or steroid-dependent inflammatory bowel disease. On the other hand, it means any dosage capable of preventing or treating an inflammatory bowel disease for which the use of a steroid preparation, an immunosuppressant, or a biological product is difficult or insufficiently effective in a patient suffering from the inflammatory bowel disease.

To both patients, adrenomedullin, a modified product thereof, or a salt thereof is preferably administered in a dosage not greatly affecting (little affecting or acceptably affecting) circulatory dynamics. The effect on circulatory dynamics can be typically monitored by subjective symptoms such as dizziness and blood pressure.

The "prevention" means preventing the occurrence of a disease. The "treatment" means suppressing the progress of a disease having occurred, alleviating a disease having occurred, and curing a disease having occurred.

The administration route for adrenomedullin, a modified product thereof, or a salt thereof is not particularly limited; they can be orally or parenterally administered. Particularly, it is preferred that they are intravenously administered, administered by enema, subcutaneously administered, intramuscularly administered, and intraperitoneally administered; most preferably, they are intravenously administered continuously for a predetermined amount of time.

The intravenous administration can be performed, for example, at a rate of about 0.1 to 150 pmol/kg body weight/min., a rate of about 0.5 to 50 pmol/kg body weight/min., or a rate of about 0.7 to 10 pmol/kg body weight/min. To avoid or reduce the effect (for example, blood pressure reduction) of the administration of adrenomedullin, a modified product thereof, or a salt thereof on circulatory dynamics, it is preferably performed at a rate of about 1.0 to 2.0 pmol/kg body weight/min., particularly preferably at a rate of about 1.5 pmol/kg body weight/min.

The administration time may be, for example, about 1 to 24 hours per day. For burden relief on a patient, it is preferably about 6 to 10 hours, more preferably about 7 to 9 hours, particularly preferably about 8 hours per day. For burden relief on a patient, the administration is also preferably performed only during the daytime.

The period of administration may be, for example, about 1 month. For burden relief on a patient, it is preferably about 7 to 21 days, particularly preferably about 14 days.

The preferred dosage regimen varies depending on various factors, such as race, sex, age, and body weight. Those skilled in the art can set an optimal dosage regimen, considering various factors.

The gene (normally, DNA) encoding adrenomedullin can be administered by a technique of so-called gene therapy. For example, for DNA encoding adrenomedullin, the amount of adrenomedullin in cells of a patient can be increased to sufficiently exert the effect of adrenomedullin, by i) administering DNA encoding adrenomedullin to a patient for expression or by ii) inserting DNA encoding adrenomedullin into cells or the like for expression and then, for example, transplanting the cells into a patient. The DNA encoding adrenomedullin can be administered, according to a common maneuver, alone or after inserting the DNA into an appropriate vector such as a plasmid vector, a retrovirus vector, an adenovirus vector, or an adenovirus-associated virus vector.

EXAMPLES

The present invention will be described below with reference to Examples. However, the present invention is not limited only to the following Examples.

1. Identification of Test Agent a) Agent under Test

General name: synthetic human adrenomedullin (a peptide which consists of the amino acid sequence of SEQ ID NO: 1 and in which Cys at position 16 and Cys at position 21 are disulfide bonded and the C-terminus is amidated)

Dosage form: 250 µg of synthetic human adrenomedullin is dissolved in 2.5 ml of a 3.75% mannitol solution and enclosed in a vial.

Storage: light-shielded and preserved at −30° C.

b) Production Method

Synthetic human adrenomedullin synthesized according to criteria comparable to those of drug manufacturing (Good Manufacturing Practice: GMP) in Peptide Institute, Inc. is purchased as a bulk. Its purity is confirmed in Department of Pharmacy, University of Miyazaki Hospital, and, if necessary, the process of repurification is further added. In the Department of Pharmacy, adrenomedullin is weighed, dissolved in 3.75% mannitol, sterilized using a sterilizing filter, and then enclosed in an ample. The ample is subjected to contamination test with naked eyes and freeze-preserved at −30° C.

c) Preparation Method

Immediately before use, the frozen agent under test is thawed at room temperature, and then a usage amount thereof is diluted with a total 40 ml of physiological saline.

2. Purity of Test Agent

The human adrenomedullin has been synthesized at purity of the order of 99.4%.

3. Setting of Dose (for Japanese)

The safety of continuous intravenous injection of adrenomedullin for 90 minutes was confirmed in 28 subjects including normal individuals. Thereafter, a test of continuous intravenous injection of adrenomedullin for 27 hours was performed in 12 subjects; however, particularly no adverse event was observed. However, a blood pressure reduction of more than 20 mmHg was observed at an adrenomedullin dose of 2.5 pmol/kg body weight/min. used in the test of continuous administration for 27 hours; thus, a course of reducing the dose (to 1.5 pmol/kg body weight/min.) was taken, considering higher safety. A test of continuous intravenous injection of adrenomedullin for 1 month has also been performed in various disease model animals, confirming the safety and efficacy thereof. In the present Examples, 2 weeks of the animal test period was set to the continuous administration period.

In experiments of administration of adrenomedullin to a colitis model, Gonzalez et al. has shown the efficacy of intraperitoneal administration of 12 µg/kg body weight of adrenomedullin and Talero, the efficacy of intraperitoneal administration of 100 ng/kg body weight thereof. The effect at 5.0 µg/kg body weight has been highest in our studies with enema administration to a large bowel artificial ulcer model, and a high effect has also been observed at 2.5 µg/kg body weight in DSS enteritis (diffuse colitis).

In animal experiments using an inflammatory bowel disease model, the curve showing the relation between the adrenomedullin dose and anti-inflammatory/mucosa-repairing effect has showed an anti-bell shape; the dose at which the effect is the highest (the optimal dose of adrenomedullin) is a low dose, which has proved not to cause blood pressure reduction. Thus, in the adrenomedullin administration, a low dose to an extent not greatly affecting circulatory dynamics is preferably used; a high dose rather makes it worse.

A difference in dose due to administration route is observed between the intraperitoneal administration and the enema administration. Accordingly, considering the data for intraperitoneal administration, 1.5 pmol/kg body weight/min. (9 ng/kg body weight/min., 4.3 µg/kg body weight/day) was now set as a dose capable of being expected to minimize blood pressure reduction and have efficacy. For burden relief on a patient, the administration was performed only during the daytime.

4. Patient

Patient: a woman in her sixties (suffering from diabetes, suspected history of tuberculosis)

Chief complaint: bloody stool

History of disease: She developed ulcerative colitis in 2007. Although steroid therapy was started during exacerbations in April 2008, steroid dependency and steroid resistance were exhibited. In April 2009, remission was induced by steroid powerful intravenous injection therapy+leucocyte apheresis therapy. Thereafter, the dose of steroid was attempted to be decreased; however, because of the difficulties thereof, an immunosuppressant (Imuran (Registered trademark), general name: azathioprine) was used in combination. (The immunosuppressant is a drug approved as a drug used for remission induction and remission maintenance for steroid-dependent Crohn's disease and remission maintenance for steroid-dependent ulcerative colitis.) However, the combined use was insufficiently effective, and then resulted in tending to aggravate symptoms. In June 2010, the steroid powerful intravenous injection therapy+leucocyte apheresis therapy was again performed; however, remission induction was not achieved. Considering the condition of the patient (advanced age, diabetes, and suspected history of tuberculosis), it is determined that the use of an immunosuppressant or a biological product should be avoided.

5. Administration Method

A peripheral intravenous line of the patient is secured to administer 1.5 pmol/kg body weight/min. of adrenomedullin with the administration schedule of 8 hours/day (9 a.m. to 5 p.m.) for up to 14 days. Blood pressure and pulse rate were continuously monitored; when a blood pressure reduction of 20 mmHg or more from blood pressure at the start of administration was observed or when adverse subjective symptoms were observed, the administration of the day is discontinued at that time. When blood pressure reduction or such subjective symptoms are repeated, the administration is attempted to be continued by reducing the dose; however, when the problem still exists or when the continuation of administration is determined to be difficult, for example, because the effect cannot be expected, the period of administration is shortened.

6. Evaluation Item

Subjective symptom, severity evaluation by endoscopic findings, or pathological evaluation by endoscopy or biopsy is typically used.

1) Improvement ratings of subjective symptoms and QOL (Visual analog scale: VAS, IBDQ)
2) Changes in physical findings (conjunctival congestion and the like)
3) Blood pressure, pulse, transcutaneous oxygen partial pressure
4) Electrocardiogram
5) Blood examination (blood count, biochemistry, various cytokines*, blood concentration of adrenomedullin*)
6) Clinical severity evaluation (DAI score or IOIBD score)
7) Severity evaluation by endoscopic findings in the large bowel (before and at the 1st week after adrenomedullin administration)
8) Pathological evaluation by large bowel endoscopy or biopsy (before and at the 1st week after adrenomedullin administration)
9) Large bowel cancer screening (before adrenomedullin administration)

Here, the DAI score (Disease activity index score) used in 6) Clinical severity evaluation is calculated from the sum of scores for the evaluation items shown in (a) to (d) below.

Figure 4:
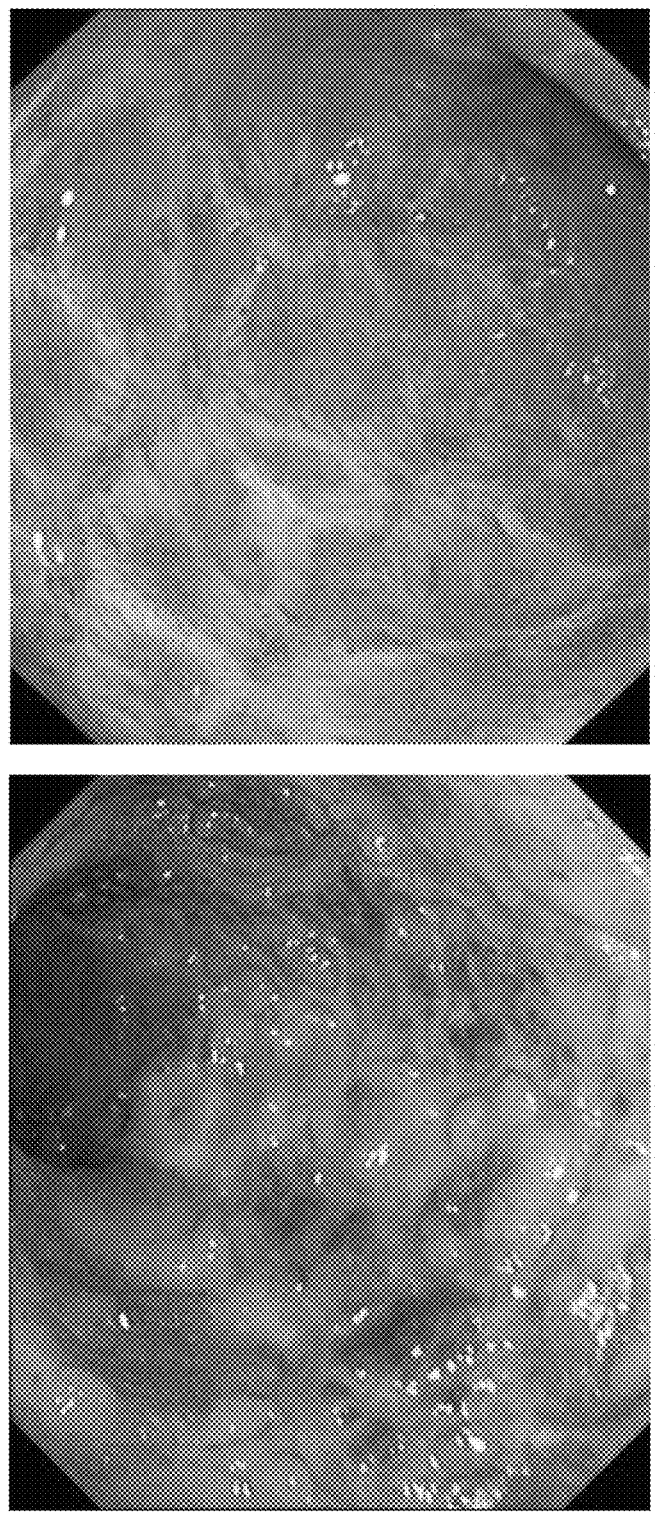
FIG. 4 is a pair of photographs showing endoscopic findings at 14 days after continuously administering adrenomedullin. In the ulcer floor of the dig deep ulcer were seen marked proliferation of regenerated epithelium (left) and scarring of shallow wide ulcer (right).

(a) Stool Frequency
0; usual, 1; additional 1 to 2 times than usual, 2; additional 3 to 4 times than usual, 3; additional 5 or more times than usual
(b) Bloody Stool
0; none, 1; slight, 2; clear, 3; only blood
(c) Endoscopic Findings
0; normal, 1; mild, 2; moderate (easy bleeding), 3; severe (spontaneous bleeding)
(d) General Evaluation by a Doctor
0; normal, 1; mild, 2; moderate, 3; severe 7. Result By endoscopic findings (FIG. 4) in the large bowel after 14 days of continuous administration of adrenomedullin, marked proliferation of regenerated epithelium and scarring of shallow wide ulcer in the ulcer floor of the dig deep ulcer were identified and remission due to adrenomedullin was confirmed. A prominent mucosal regeneration effect was confirmed compared to that in mucosal cure by a common treatment. During the period, symptoms and the like considered to be side effects were not observed, and the effect on circulatory dynamics was also within a sufficiently acceptable range (blood pressure reduction: 10 mmHg or less).

Variation in the blood concentration of adrenomedullin immediately after administration was smaller than variation due to inflammation, and it is advantageous as a drug to exert an effect by a very small dose of administration.

Figure 6:
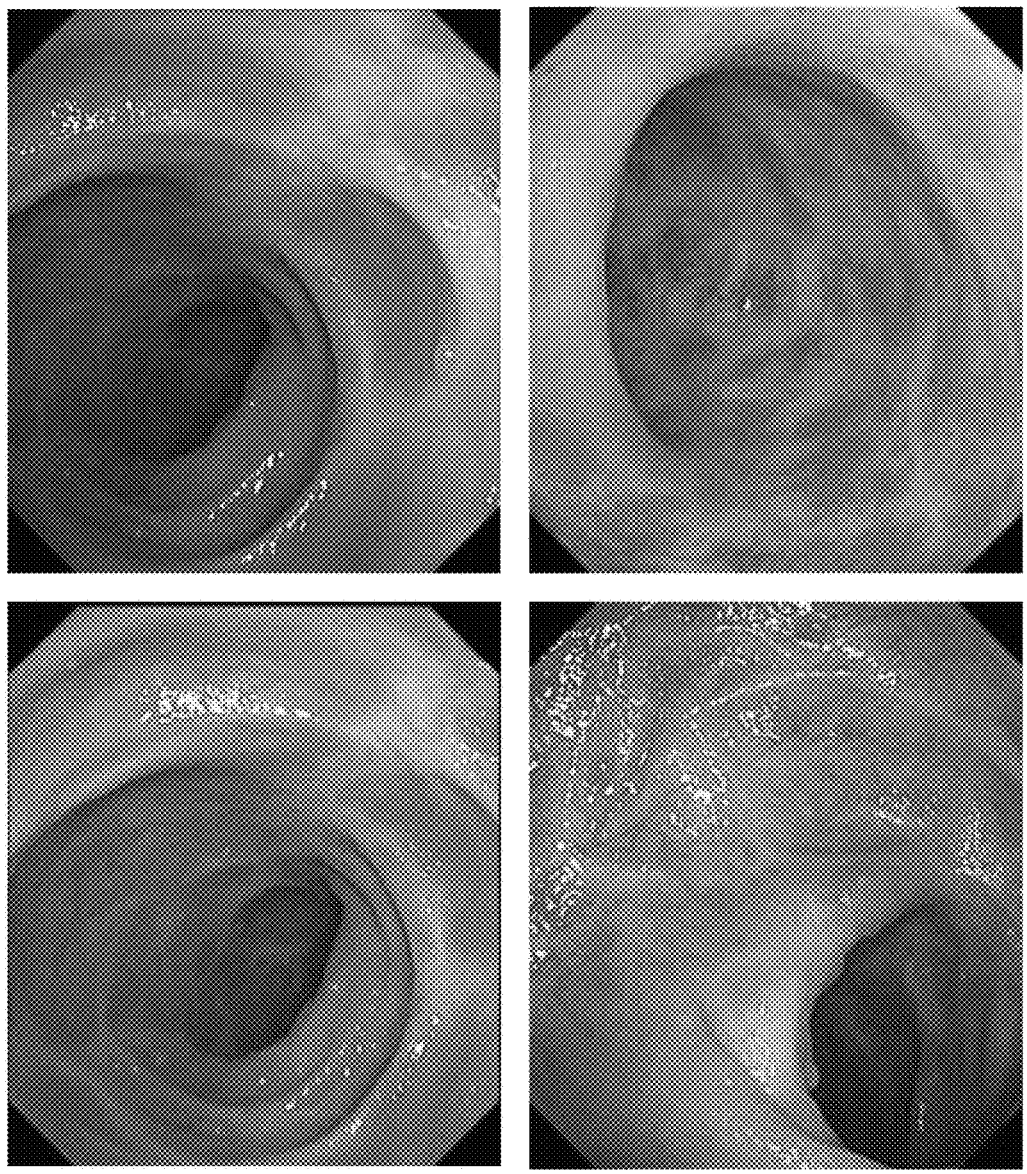
FIG. 6 is a set of photographs showing endoscopic findings after a lapse of 3 months from the continuous administration of adrenomedullin. Remission maintenance was confirmed.

Because remission by adrenomedullin administration was confirmed, 50 mg/day of azathioprine was afterward administered for continuation treatment to try to maintain the remission. Endoscopic findings (FIG. 6) in the large bowel after a lapse of 3 months after adrenomedullin administration confirmed the maintenance of the remission. Endoscopic findings in the large bowel after a lapse of 12 months after adrenomedullin administration also confirmed the maintenance of the remission.

In addition to this patient, patients in their thirties to sixties received the administration of adrenomedullin by the administration method described in "5. Administration Method" above. All administration cases including the patient described in "4. Patient" above are shown in Table 1.

TABLE 1

| | |
|---|---|
| Total Number of Cases | 6 |
| Age | 30 s to 60 s |
| Number of Cases by Sex | Male 3, Female 3 |
| Number of Cases by Disease Severity on Admission | Severe 2, Moderate 4 |
| Number of Cases by Severity before Adrenomedullin Administration | Moderate 6 |
| Number of Cases by Intractability | Steroid-Resistant 3 Steroid-Dependent 1 Steroid-Resistant and Steroid-Dependent 2 Note: Of all 6 cases, there are 2 azathioprine-intolerant cases. |
| Number of Cases by Continuation Treatment after Adrenomedullin Administration | Tapering of PSL 5 Azathioprine Administration 3 LCAP 2 Note: Overlap exists. |

Figure 5:
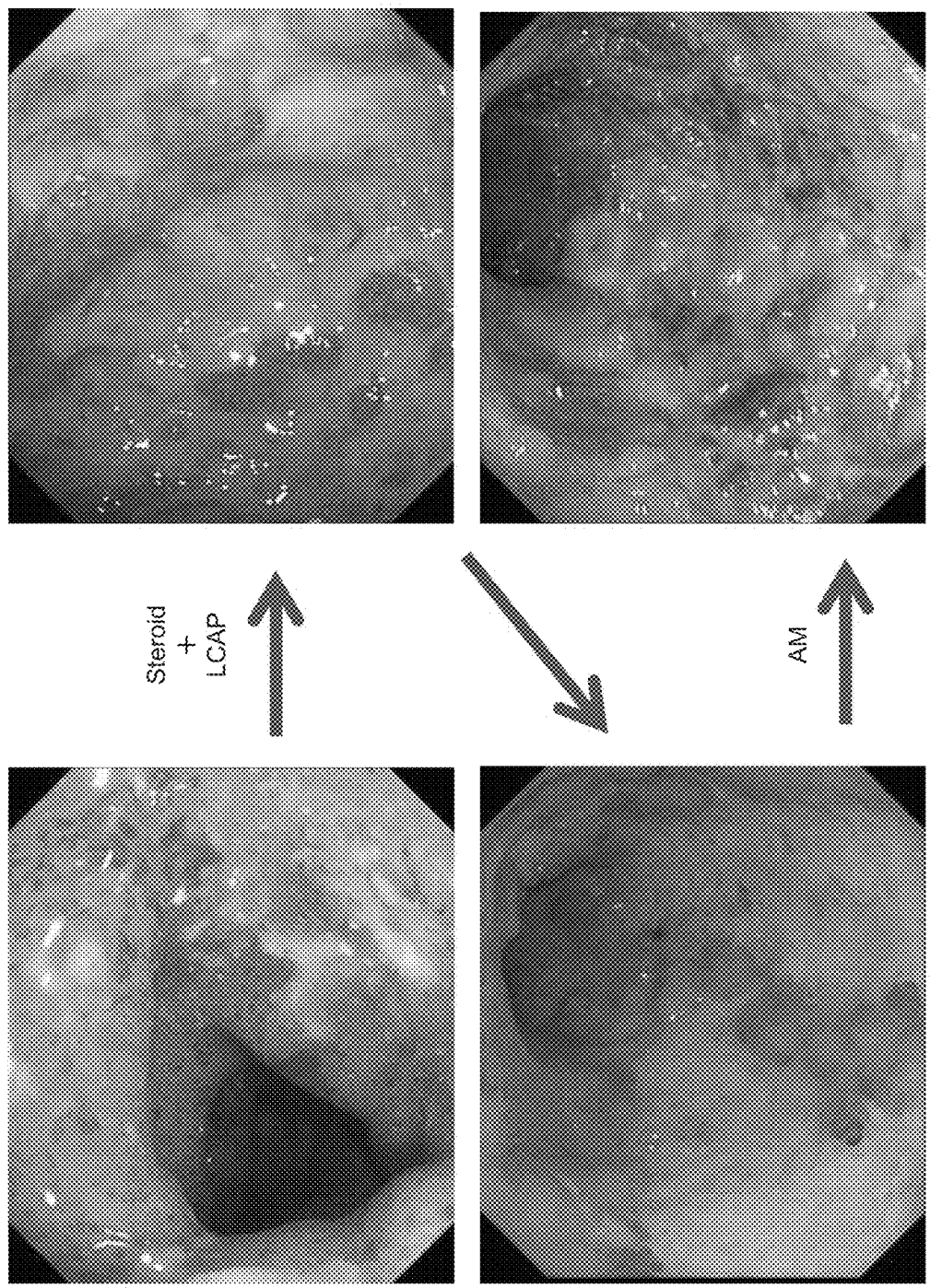
FIG. 5 is a set of photographs of endoscopic findings showing changes in endoscopic findings of FIGS. 1 to 4.

The treatment effects are shown in Table 2 using DAI (* in the table indicates p<0.05). DAI at the time of a lapse of 14 days after adrenomedullin administration improved 4 points or more in 4 cases and 1 to 3 points in 2 cases. Thus, the treatment effects were confirmed in all cases of adrenomedullin administration. In all cases, as in FIGS. 4 to 6, prominent mucosal regeneration was also confirmed in the affected areas, and remission was maintained.

TABLE 2

| | DAI (Average) | p (vs. Immediately before Adrenomedullin Administration) |
|---|---|---|
| On Admission | 10.8 ± 1.2 | 0.8960 |
| Immediately before Adrenomedullin Administration | 9.0 ± 1.4 | — |
| Adrenomedullin Administration (14 Days after Start of Administration) | 5.0 ± 2.4 | 0.0028* |
| Adrenomedullin Administration (12 Weeks after Start of Administration) | 1.0 ± 1.15 | 0.0001* |

All publications, patents, and patent applications cited in this specification are intended to be incorporated herein by reference in their entirety.

The invention claimed is:

1. A method for alleviating or suppressing the progress of a steroid-resistant or steroid-dependent inflammatory bowel disease in a patient afflicted with the disease comprising administering to the patient an effective amount of adrenomedullin, a modified product thereof or a salt of the adrenomedullin or the modified product, each of which has an activity of suppressing inflammation in the patient, thereby alleviating or suppressing the progress of the steroid-resistant or steroid-dependent inflammatory bowel disease in the patient, wherein the alleviating or suppressing the progress of the steroid-resistant or steroid-dependent inflammatory bowel disease in the patient comprises mucosal regeneration.

2. The method according to claim 1, wherein the adrenomedullin or the modified product is a peptide selected from the group consisting of the following (i) to (vi):
   (i) a peptide consisting of the amino acid sequence of adrenomedullin;
   (ii) a peptide consisting of the amino acid sequence of adrenomedullin whose two intramolecular Cys are disulfide bonded;
   (iii) a peptide of (ii) in which the disulfide bond is substituted with a —CH$_2$—CH$_2$— bond;
   (iv) a peptide of any of (i) to (iii) having deletion, substitution, or addition of 1 to 15 amino acids and having an activity of suppressing inflammation;
   (v) a peptide of any of (i) to (iv) whose C-terminus is amidated; and
   (vi) a peptide of any of (i) to (iv) having addition of Gly at the C-terminus.

3. The p method according to claim 1, wherein the adrenomedullin or the modified product is a peptide selected from the group consisting of the following (a) to (j):
   (a) a peptide consisting of the amino acid sequence of SEQ ID NO: 1, or a peptide consisting of the amino acid sequence of SEQ ID NO: 1 in which Cys at position 16 and Cys at position 21 are disulfide bonded;
   (b) a peptide consisting of the amino acid sequence of SEQ ID NO: 3, or a peptide consisting of the amino acid sequence of SEQ ID NO: 3 in which Cys at position 16 and Cys at position 21 are disulfide bonded;
   (c) a peptide consisting of the amino acid sequence of SEQ ID NO: 5, or a peptide consisting of the amino acid sequence of SEQ ID NO: 5 in which Cys at position 16 and Cys at position 21 are disulfide bonded;
   (d) a peptide consisting of the amino acid sequence of SEQ ID NO: 7, or a peptide consisting of the amino acid sequence of SEQ ID NO: 7 in which Cys at position 16 and Cys at position 21 are disulfide bonded;
   (e) a peptide consisting of the amino acid sequence of SEQ ID NO: 9, or a peptide consisting of the amino acid sequence of SEQ ID NO: 9 in which Cys at position 14 and Cys at position 19 are disulfide bonded;
   (f) a peptide consisting of the amino acid sequence of SEQ ID NO: 11, or a peptide consisting of the amino acid sequence of SEQ ID NO: 11 in which Cys at position 14 and Cys at position 19 are disulfide bonded;
   (g) a peptide of any of (a) to (f) in which the disulfide bond is substituted with —CH$_2$—CH$_2$— bond;
   (h) a peptide of any of (a) to (g) having deletion, substitution, or addition of 1 to 15 amino acids and having an activity of suppressing inflammation;
   (i) a peptide of any of (a) to (h) whose C-terminus is amidated; and
   (j) a peptide of any of (a) to (h) having addition of Gly at the C-terminus.

4. The method of claim 1, wherein the adrenomedullin, the modified product, or the salt is intravenously administered continuously.

5. The method of claim 1, further comprising determining that a steroid preparation, an immunosuppressant, or a biological product is insufficiently effective for preventing or treating the inflammatory bowel disease in the patient.

6. The method of claim 1, wherein the administering is at a rate of 1.5 pmol/kg body weight/min for 8 hours per day for 14 days.

7. The method of claim 1, wherein the patient is a human.

8. The method of claim 1, wherein the alleviating or suppressing the progress of the steroid-resistant or steroid-dependent inflammatory bowel disease in the patient comprises improving a disease activity index (DAI) score of the patient by four points or more.

9. The method of claim 1, wherein the alleviating or suppressing the progress of the steroid-resistant or steroid-dependent inflammatory bowel disease in the patient comprises proliferation of regenerated epithelium.

10. The method of claim 1, wherein the administering is at a rate of 1.0 to 2.0 pmol/kg body weight/min for 6 to 10 hours per day for 7 to 21 days.

* * * * *